United States Patent
Sumathipala (10) Patent No.: US 9,885,663 B2
(45) Date of Patent: Feb. 6, 2018

(54) PORTABLE, RAPID, AND INEXPENSIVE DIAGNOSTIC TESTS FOR CARDIAC DISEASE RISK

(71) Applicant: Adriel Sheehan Sumathipala, Ashburn, VA (US)

(72) Inventor: Adriel Sheehan Sumathipala, Ashburn, VA (US)

(73) Assignee: Adriel Sumathipala, Ashburn, VA (US)

( * ) Notice: Subject to any disclaimer, the term of this patent is extended or adjusted under 35 U.S.C. 154(b) by 0 days.

(21) Appl. No.: 14/922,172

(22) Filed: Oct. 25, 2015

(65) Prior Publication Data
US 2017/0115228 A1    Apr. 27, 2017

(51) Int. Cl.
*G01N 33/92* (2006.01)
*G01N 21/78* (2006.01)
*G01N 21/84* (2006.01)
*G01N 21/77* (2006.01)

(52) U.S. Cl.
CPC ......... *G01N 21/78* (2013.01); *G01N 21/8483* (2013.01); *G01N 2021/7759* (2013.01)

(58) Field of Classification Search
CPC ......... G01N 2333/90267; G01N 33/92; G01N 2021/7759; C12Q 1/68
USPC ............. 427/2.1, 2.11, 2.12, 2.13; 435/6, 11
See application file for complete search history.

(56) References Cited

U.S. PATENT DOCUMENTS

| | | | | |
|---|---|---|---|---|
| 4,478,942 A * | 10/1984 | Katsuyama | ............... | C12Q 1/28 422/421 |
| 5,541,115 A * | 7/1996 | Siegel | ...................... | C12Q 1/28 436/135 |
| 6,040,195 A * | 3/2000 | Carroll | ................. | G01N 33/525 422/408 |
| 7,504,235 B2 * | 3/2009 | Song | ........................ | C12Q 1/44 435/19 |
| 2002/0064781 A1 * | 5/2002 | Lyles | ...................... | B29C 41/16 435/6.12 |
| 2004/0053352 A1 * | 3/2004 | Ouyang | ................... | C12Q 1/26 435/25 |

(Continued)

OTHER PUBLICATIONS

Wilson et al. A low Cost Ink-Jet Printed Glucose Test Strip System for Resource Poor Settings. Journal of Diabetes Science and Technology. 2015 vol. 6 (6) 1257-1281.*

(Continued)

*Primary Examiner* — Cachet I Sellman (57) ABSTRACT

Cardiac disease is the world's leading cause of death. Cardiac Disease's pathogenesis is largely attributed to cholesterol, predominantly carried by low-density lipoproteins (LDL). However, recent research has found that oxidized-LDL is significantly more potent in the initiation and development of atherosclerosis. Tests for both cholesterol and ox-LDL tests are lab-based and expensive. With every third American at risk for Cardiac Disease, this invention discloses an on-site, ultra-low cost, rapid diagnostic test. The diagnostic test disclosed will enable a holistic assessment of Cardiac Disease risk. Furthermore, portability and ultra low-cost of the test put vital health data in the hands of patients and doctors. Additionally, the inkjet printing system disclosed can be used to mass produce the test strips on demand.

1 Claim, 6 Drawing Sheets

Schematic diagram of the preparation of the detector strip using an inkjet printer.

(56) References Cited

U.S. PATENT DOCUMENTS

2005/0164406 A1* 7/2005 Carroll ................. G01N 33/525
                                                      436/514
2011/0136269 A1* 6/2011 Du .................... H01J 37/32935
                                                      438/7

OTHER PUBLICATIONS

Creran et al. Detection of Bacteria Using InkJet Printed Enzymatic Test Strips. ACS APplied Materials and Interfaces. 2014. vol. 6 pp. 19525-19530.*

Setti et al. An Amperometric glucose biosensor prototype fabricated by thermal inkjet printing. Biosensors and Bioelectrics. vol. 20, Issue 10 Apr. 2015 pp. 2019-2026.*

* cited by examiner

Figure 1: Schematic diagram of the preparation of the detector strip using an inkjet printer.

Figure 2: Schematic diagram of prototype detector, before and after use.

Figure 3: Side view schematic depiction of test strip layers, including printed reagent mixture and color detection reagent Figure 4: Variation of color intensity with concentration of low density lipoprotein in the presence of Tetramethylbenzadine as the color detection reagent Figure 5: Variation of color intensity with concentration of low density lipoprotein in the presence of 4-Aminoantipyrene Dye as the color detection reagent Figure 6: Variation of color intensity with concentration of low density lipoprotein in the presence of Amplex Red as the color detection reagent

PORTABLE, RAPID, AND INEXPENSIVE DIAGNOSTIC TESTS FOR CARDIAC DISEASE RISK

FIELD OF THE INVENTION

The present invention relates generally to reagents and methods for detecting cardiac heart disease which are capable of measuring low density lipoprotein as well as oxidized low density lipoprotein in a sample, including a blood sample. The method utilizes reagents to convert the lipoproteins into hydrogen peroxide in a sample on a substrate surface. In one aspect, the method of applying the reagents onto the substrate by repurposing two types of commercial inkjet printers, a piezoelectric printer and a thermal bubble jet printer, is provided. A method for producing rapid diagnostic of the lipoproteins that is much lower cost compared to conventional diagnostic assays and practices in provided.

BACKGROUND OF THE INVENTION

US Patent application US 2012062436A2, by Abner D. Joseph, disclose an inkjet deposition for biosensor manufacturing. However, there is a need for a rapid and inexpensive diagnostic test for risk of cardiac heart disease assessment. Cardiovascular disease is the preeminent cause of morality in the world, more so than cancers, respiratory ailments, or infectious diseases. Cardiovascular disease is expensive to treat and much cheaper to prevent if the patients had a way to identify their risk level. This invention makes it possible for early diagnosis as well as quantification of the risk level.

Similar to other diseases that require long term treatment, such as, HIV and cancer, detection of cardiovascular disease is essential for successful treatment. Additionally, the treatment is individual-specific and require continuous monitoring of the risk level. The invention described here allow for a fast, portable, and inexpensive diagnostic method.

Present diagnostics for cardiac disease are lab-based, require large sample volumes, expensive, take long time to report results, and are, as a result, infrequently conducted. As a result many high-risk patients are often unaware of their risk level and the possible need for lifestyle changes to lower their risk level.

SUMMARY OF THE INVENTION

The invention relates generally to reagents, methods, and diagnostic test strips for detection of low density lipoprotein and oxidized low density lipoprotein. In a particular aspect of the invention, methods and diagnostic test strips are provided for the detection of lipoproteins of interest. The invention further relates to reagents and methods for quantitative measurement of the lipoproteins of interest in a sample. In one aspect, reagents and methods for diagnostic assay for lipoproteins is provided. The reagents include: Horseradish Peroxidase, Cholesterol Oxidase, Glycerol, and one of three dyes, a) Tetramethylbenzidine, b) dihydroxyphenoxazine, or c) 3 4-Aminoantipyrine.

The invention provides a system for the detection and quantification of lipoproteins of interest in a sample; the said system comprising of:
(A) a substrate or solid support suitable for being passed through an ink jet printer and is capable of absorbing the applied reagents;
(B) a set of reagents to be applied via a repurposed inkjet printer bound covalently or non covalently to the substrate or support of (A) and applied in varying patterns and of varying concentrations or dilutions;
(C) a rheology of reagents such that the repurposed inkjet printer is capable of applying the reagents to the substrate and is capable of binding directly or indirectly with the substrate and other reagents already present on the substrate or support of (A) and;
(D) an indicator means which indicates the amount of lipoprotein of interest, whereby the presence and amount of lipoprotein of interest in the sample is indicated.

In one embodiment of the invention the system is further characterized by the following:
(E) the substrate or solid support is a wickable medium;
(F) a set of reagents is applied in the patter of a circle via a repurposed inkjet to the substrate or support of (A) at a select concentration; and
(G) a color indicator reagent is used to provide a the amount of lipoprotein of interest along with a digital camera to capture and digitize the color image to detect and quantify the amount of lipoprotein of interest.

DETAILED DESCRIPTION

Cardiovascular disease is the preeminent cause of morality in the world, more so than cancers, respiratory ailments, or infectious diseases. Cardiovascular disease killed an estimated 17.5 million people in 2012, or 31% of all global deaths, according to the World Health Organization (WHO). In the United States alone, cardiovascular disease is responsible for every third death, claiming more lives than all cancers combined. Moreover, cardiovascular disease is a problem in both developing and developed states with 80% of cardiovascular disease deaths occurring in low to middle income countries (GDP/capita>$10,066), at younger ages than in high-income countries. Low to middle income states' (LIMC) are resource poor environments with largely undeveloped healthcare infrastructures and limited resources. This exacerbates the regional impacts of cardiovascular disease in LIMCs.

Compounding its global presence in both LIMCs and developed states, cardiovascular disease is an expensive disease to treat, costing the United States alone 444 billion dollars annually to treat, with each incidence of cardiovascular arrest costing an average of $760,000 to treat. This equates to one out of every six dollars spent on health care in the United States. In LIMCs the WHO estimates, given current spending and accounting for inflation, cardiovascular disease treatment will cost 3.76 trillion dollars to treat from 2011-2025; considering the costs of treatment, the WHO and American Heart Association advocate that early diagnosis and lifestyle changes are the most economically prudent policy to combat cardiovascular disease.

Like HIV and cancer, early detection of cardiovascular disease is essential so that long-term treatment can begin to improve quality of life and reduce risk of death. There is no single, simple treatment for cardiovascular disease. Cardiovascular disease is best treated through long-term lifestyle management. Patients who seek to manage, and monitor their risk for cardiovascular disease, need rapid, accurate, portable multi-biomarker risk assessment diagnostic that gives feedback on lifestyle management. These diagnostics must be portable enough to be used in non-labors Moreover, in LIMCs, which lack the infrastructure needed to run the current diagnostic, inexpensive diagnostics are needed to diagnose cardiac disease.

Present diagnostics for cardiac disease are lab-based, require large sample volumes, expensive, take long time to report results, and are, as a result, infrequently conducted. As a result of the resource-intensive nature of current cardiac disease diagnostics, cardiovascular disease often goes undiagnosed in LIMCs with undeveloped healthcare infrastructures, and in developed states, tests for cardiovascular disease risk are run infrequently, generally once every six months. Current lab-based tests, in addition to aforementioned deficiencies, use complex procedures such as the multi-step sandwich enzyme-linked immunosorbent assays (sandwich ELISAs) which necessitate specialized lab equipment and trained lab specialists. Finally, standard lab tests target a single biomarker: cholesterol, in a variety of lipoprotein molecule (ex: high, low, and very low-density lipoproteins.)

In view of the aforementioned time, portability, and cost deficiencies associated with prior art diagnostics, testing and methods, it should be apparent that there exists a great need in the art for inexpensive, rapid, portable, diagnostics that incorporate information from multiple biomarkers associated with cardiovascular disease. Furthermore, an economically prudent method to manufacture the diagnostic and a mobile platform to analyze and quantify the diagnostic's results are needed. Finally, the diagnostic and quantification device must be portable and simple enough for non-specialists, including but not limited to patients, and care providers, to use in a variety of settings, including but not limited to homes, offices, and point-of-care settings.

As noted in prior art, the traditional approaches for applying reagent to diagnostic test strips, such as traditional slot-die coating, drop deposition techniques, and screen or rotary printing techniques, have some significant drawbacks, such as manufacturing line speed limitations, quality issues, and reagent waste, to name a few. These inherent limitations in traditional production of test strip production can be overcome by inkjet printing of the reagents.

Figure 1:
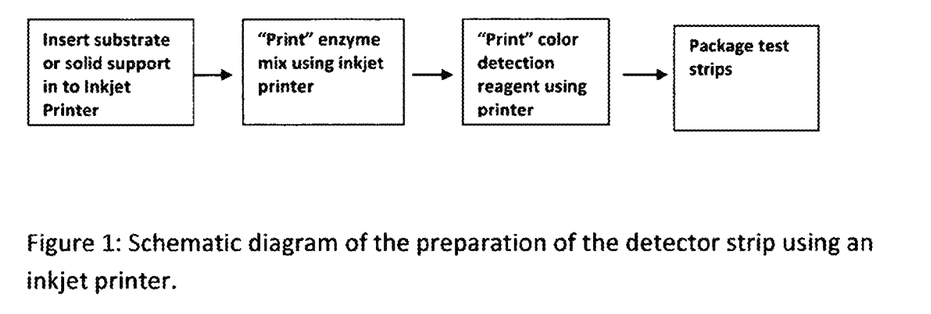
FIG. 1: Shows the schematic diagram of the preparation of the detector strip using inkjet printer.

The invention described here was able to overcome several significant obstacles in order to produce commercially viable diagnostic test strips for detection of cardiac heart disease using the inkjet printing technique. This invention describes a commercially-viable formulation for inkjet printing of diagnostic test strips. FIG. 1 shows the schematic of the detector strip development. As shown, the test strip substrate or solid support is placed in the inkjet printer paper tray. Enzyme mixture is than placed in the inkjet printer ink cartridge. Pre determined shape of the enzyme ink is then printed on to the test strip substrate. Color detection reagent is then placed in the inkjet printer ink cartridge. Pre determined shape of the color detection reagent then printed over the enzyme ink print on to the test strip substrate.

Figure 2:
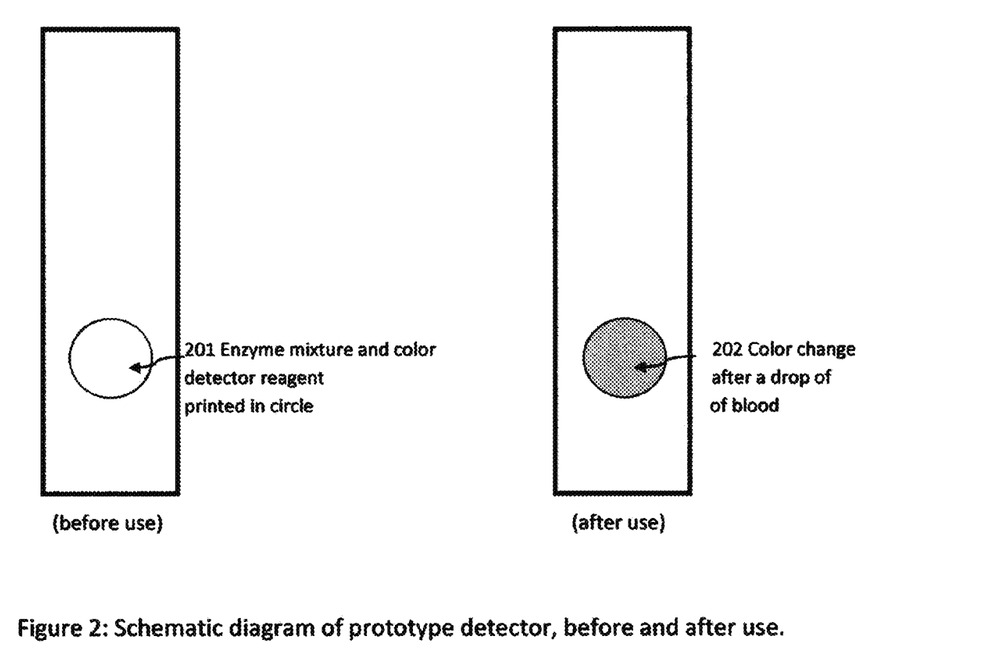
FIG. 2: Shows the schematic diagram of the prototype detector, before and after diagnosis.
201—enzyme mixture and color detector printed as a circle on the substrate or solid support
202—enzyme mixture and color detector change in color when a sample of blood is introduced.

The invention enables production of diagnostic test strips with a wide variety of patterns for diverse use. It also enables printing of different reagent formulations on the same test strip for detecting multiple diseases. Additionally, the technique allows for multilayer printing with reagents in different layers. Shape, thickness, and number of layers of reagents can be easily configured by changing the printing pattern on a computer. This ability to swiftly reconfigure the test strips avoids retooling and machine stoppages required in the traditional approaches for developing diagnostic test strips. FIG. 2 shows the schematic of the detector strip before and after diagnosis use. As indicated by 201, the enzyme mixture and color detector are printed as a circles on the substrate or solid support. While a circular shape of printed enzyme mixture and color detector is shown other shapes and sizes are just as easily printed. Once a small sample of blood is placed over the enzyme mixture n the detection strip the color changes introduced to the 202 shows the enzyme mixture and color detector change in color when a sample of blood is introduced.

Figure 3:
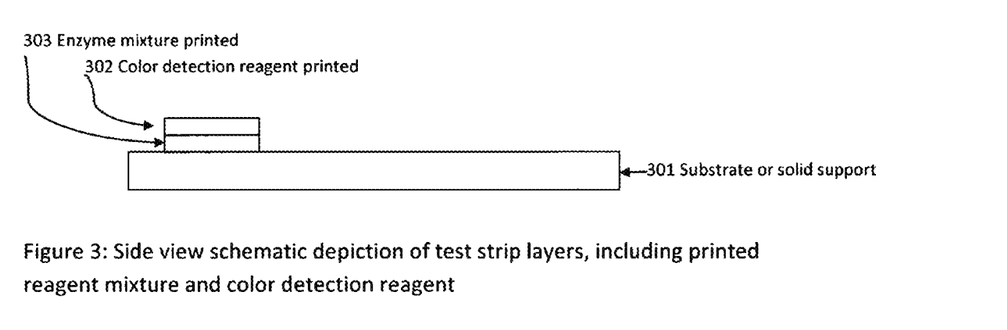
FIG. 3: Shows the side view schematic depiction of test strip layers, including printed reagent.
301—enzyme mixture layer is printed first on the substrate or solid support
302—color detection reagent printed on top of the enzyme mixture

Inkjet printing, however, requires a more robust formulation for the reagent so as to minimize impact on the reagent activity of the enzymes. This invention was able to overcome several significant obstacles in order to produce formulation that was able to overcome this limitation in reagent activity. FIG. 3 shows one embodiment of the present invention where a layer of enzyme mixture (303) is first applied by an inkjet printer on the substrate (301). The color detection reagent (302) is then applied by the inkjet printer on top of the enzyme mixture. It should not, however, be considered a limitation of the scope of the invention that the enzyme mixture and color detection reagent are applied as two separate layers (302 and 303, respectively) on the substrate. The enzyme mixture and color detection reagent may be applied as one mixture or multiple layers. The provided FIGS. 1 through 3 show one embodiment of the present invention. It should not, however, be considered a limitation of the scope of the invention. Any alterations and further modifications in the described processes or devices by one skilled in the art, and any further applications of the principles of the invention as described herein are considered a part of this invention. For example, the substrate or solid surface onto which reagents are applied by inkjet printing can be a flat surface or may have depressions, such as, indentations, groves, wells, etc. Such depressions can be created by multilayer substrate where cutouts have been formed on some of the layers. The depositing of reagents into such depressions on a substrate can be accomplished by conveniently reprogramming the computer driving the inkjet printer. Inkjet printers produce droplets in the range of 2 to 4 Pico liters giving the ability to apply reagents uniformly and also to control the reagent film thickness precisely. This enables the development of accurate and repeatable diagnostic test strips. This technique allows for printing an active reagent as the first layer and a platelet separating polymer as a second layer. This allows for separating relatively larger sized white and red blood cells from proteins in blood, such as, oxidized Low Density Lipoprotein. An embodiment allowing for separation of red blood cells from blood proteins prior to reacting with the enzyme mixture would increase the accuracy of colorimetry to detect oxidized-LDL.

Figure 4:
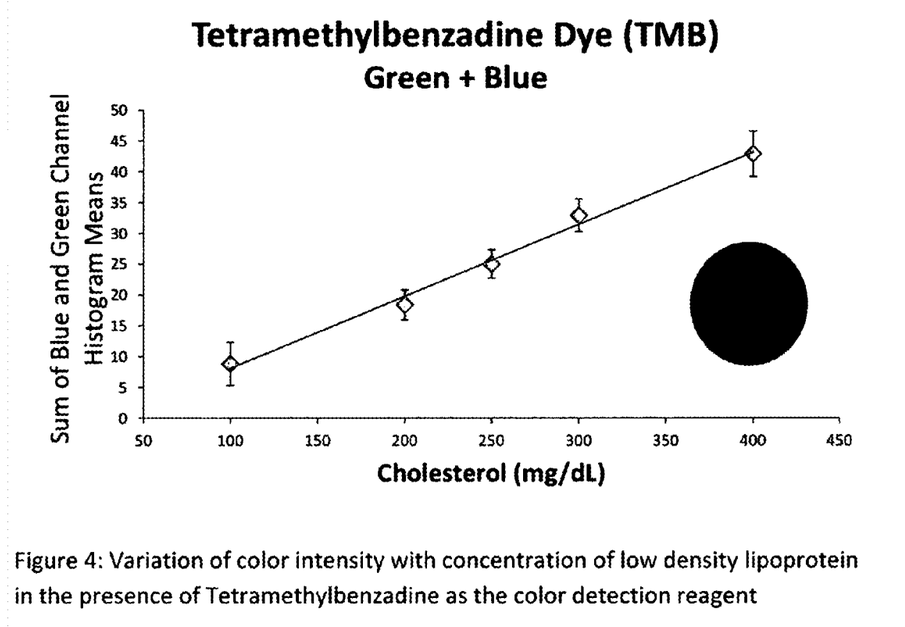
FIG. 4: Shows the variation of color intensity with concentration of low density lipoprotein in the presence of Tetramethylbenzadine as the color detection reagent. The color intensity was measured by smart phone digital photography. The data shows the average of green and blue color intensity values. The error bars indicate the small variation of color intensity measured in multiple test strips.
Figure 5:
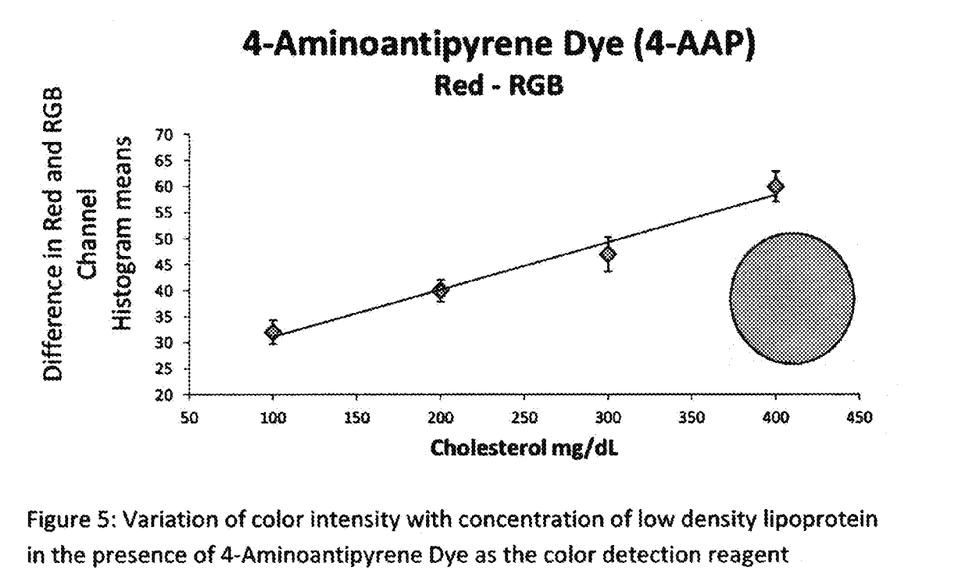
FIG. 5: Shows the variation of color intensity with concentration of low density lipoprotein in the presence of 4-Aminoantipyrene Dye as the color detection reagent. The color intensity was measured by smart phone digital photography. The data shows the difference between the red and average of RGB intensity values. The error bars indicate the small variation of color intensity measured in multiple test strips.
Figure 6:
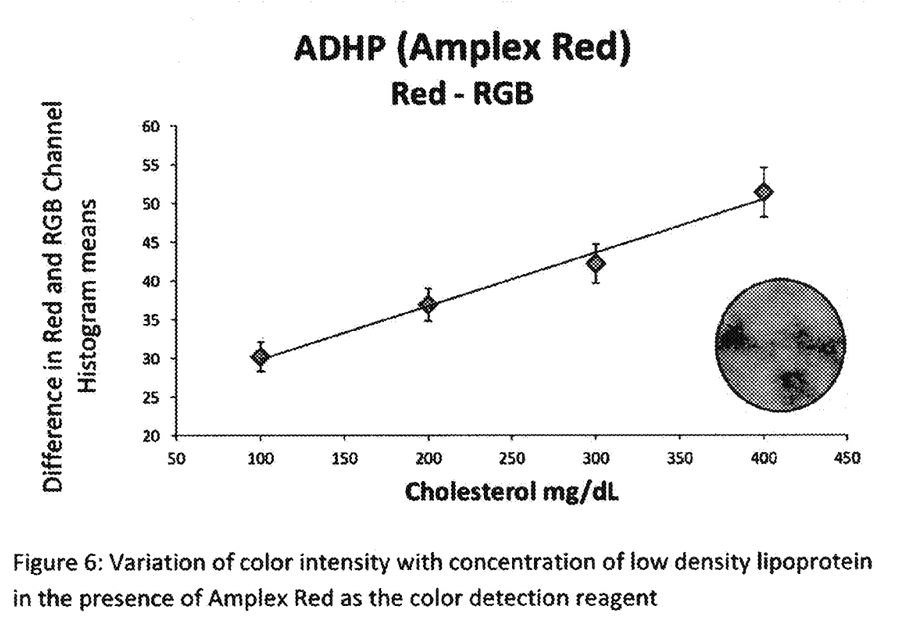
FIG. 6: Shows the variation of color intensity with concentration of low density lipoprotein in the presence of 10-Acetyl-3,7-dihydroxyphenoxazine, commonly referred to as Amplex Red, as the color detection reagent. The color intensity was measured by smart phone digital photography. The data shows the difference between the red and average of RGB intensity values. The error bars indicate the small variation of color intensity measured in multiple test strips.

FIGS. 4 through 6 show the results obtained for four different concentrations of LDL using three common color detection reagents, tetra methylbenzene (TMB), 4-aminoantipyrene, and 10-Acetyl-3,7-dihydroxyphenoxazine (ADHP), respectively. The latter is commonly referred to as Amplex Red. As shown, all three color detection reagents were able to quantify the LDL concentrations in the rage 100 to 400 milligrams per deciliter, the typical range for LDL in human blood. The color separation histograms in FIGS. 4 through 6 were obtained from photography using a smart phone.

Several workable enzyme mixture and color detection reagent suitable for inkjet printing are disclosed below. All of them can be applied as a single mixture ink formulation on a substrate or solid support, or as two separate layers on a substrate or solid support. If applying as two separate layers the results are best when the enzyme mixture is applied first, followed by the color detection reagent.

Reagent Ink Formulation

When developing the reagent ink, a number of significant factors and issues were overcome. Several factors of ink rheology affected the thickness and uniformity of the printed reagent film. Inkjet printing rheology has much narrow limitations than for traditional methods of slot-die coating or screen printing. Specifically, inkjet printing requires high shear thinning and has to be within a narrow range of ink viscosity. For example, bubble thermal jet printers operate with ink formulations in the range of 1-3 cP viscosity, whereas piezo-electric inkjet printing ink works best in a viscosity range of 6-12 cP. In either method, the enzyme formulation should be able to withstand the shear produced by the inkjet head without losing activity.

This invention describes the addition of glycerol as a surfactant to address both the needed reduction on surface tension as well as ink rheology of reagent ink to be printable with an inkjet printer. While other types of surfactants may work inclusion of ionic surfactants tend to degrade enzyme activity. Additionally, glycerol provided fast wetting of the substrate and control of dispersal of reagent ink. Reagent ink formulations with high surface tension tend to deposit reagent ink that is not mixed properly. Reagent ink with low surface tension tends to spread beyond the area of printing. Neither condition produces a desirable test strip.

Materials and Methods

An embodiment of repurposing a piezoelectric inkjet printer and a bubble thermal inkjet jet printer is disclosed. Also disclosed is ink formulation that works well in commercial production, using either type of printer, to produce test strips for detection of cardiac heart disease.

Printer Type: Epson WorkForce 30 Inkjet Piezoelectric Printer

1. Epson WorkForce 30 ® Inkjet Piezoelectric Printer
   i. Cartridge Preparation
      1. Refillable ink cartridges were purchased from online retailers
      2. Two methods were used to charge the cartridge
         a. Direct charging
            i. Enzyme ink was injected directly into the cartridge
            ii. Air was pipetted into the cartridge to fill a circular air chamber and pressurize the cartridge
         b. Indirect charging
            i. Air was pipetted into the cartridge to fill a circular air chamber and pressurize the cartridge
            ii. Surgical tubing was secured to the cartridge's ink opening
            iii. Enzyme ink was pipetted directly into the tubing
      3. Only one of five ink cartridges (black, black, cyan, magenta, and yellow) was used during printing
      4. The four remaining ink cartridge slots were filled by empty cartridges or a pseudo-cartridges that deceived the printing electronics into accepting a cartridge identifier chip
   ii. Printer Preparation
      1. The printer's covering assembly was removed, exposing the cartridges, rails, and electronics below
      2. The printer's clamping paper sensor was secured shut to delude the printer into printing smaller sheets of paper
      3. The peripheral power and printer cables were attached to a PC and necessary drivers were installed to
   iii. Printing
      1. Open-source vector graphics editor, Inkscape, was used to define printing regions using colors that corresponded to and activated single ink cartridges
      2. Printed at max DPI
      3. To ensure the functionality of both the printer assembly and the printhead a blank ink (Glycerol and H2O) was printed at various concentrations
      4. To further confirm the viability of the printing apparatus, a UV-fluorescent substrate, fluorescein, was added to the blank ink
         a. The resultant printing sample was then promptly viewed in a UV cabinet
      5. Reagent was printed onto Whatman grade 1 filter paper (4"×6")
      6. The paper test strip was then tested with known cholesterol concentrations, its color change photographed, and the image analyzed (below)
2. HP Deskjet 1010 ® Bubble Thermal Inkjet Printer
   i. Cartridge Preparation
      1. The sensitive and delicate electronics and printhead of the cartridge were shielded from the external environment
      2. An even cut approximately ⅛" from the top of the cartridge was made across its entirety, thus exposing the primary ink chamber
      3. An ink-soaked sponge was removed from the primary ink chamber with forceps
      4. Ink was expunged from the cartridge a. A Kimwipe® was inserted into the cavity to soak up residue ink
　　b. Isopropyl alcohol (70%) and ethanol (99%) was sprayed into the cavity
　　c. A Kimwipe® was manipulated with forceps until saturated
　　d. Steps B and C were repeated until the no ink was present on the Kimwipe® after cleaning (about 60-70×)
　5. A filter separating the primary ink chamber from the secondary ink chamber was removed
　6. The newly exposed secondary ink reservoir was filled isopropyl alcohol (70%) and ethanol (99%)
　　a. The solution was then pipetted vigorously to cleanse the interior of the secondary ink reservoir
　　b. Finally the solution, in its entirety was pipetted out of the reservoir
　　c. The above step (6) was repeated until the alcohol and ethanol solution was no longer soiled by ink
　7. The cartridge was left to dry at room temperature for an hour
　8. The cartridge was placed in a sonicator for 10 minutes, wiped clean, and left to dry for an hour
ii. Pre-printing Cartridge Preparation
　1. A warm dH2O and surfactant solution was prepared
　2. Said surfactant/dH2O solution was sprayed into the primary and secondary chambers, and onto the printhead of the cartridge
　3. The cartridge was rinsed in dH2O to remove surfactant solution
　4. Ethanol (99%) was then deposited into the primary and secondary chambers of the cartridge
　5. Kimwipes® manipulated with forceps, then absorbed the Ethanol cleaning solution
　6. Steps (4,5) were repeated 5×
iii. Printer Preparation
　1. Covering assembly was removed
　2. Paper feeder was removed to allow smaller paper dimensions to be inserted
iv. Printing
　1. Open-source vector graphics editor, Inkscape, was used to define printing regions using colors that corresponded to and activated single ink cartridges
　2. Printed at max DPI (1200×1200)
　3. To ensure the functionality of both the printer assembly and the printhead a blank ink (Glycerol and H2O) was printed at various concentrations
　4. Reagent was printed onto a solid substrate. Whatman grade 1 filter paper was suitable for the purpose
　5. After a brief period of drying the test strip is ready for commercial use.

Enzyme Ink

The test strips were produced by first making the following reagent mixes that were then placed in the inkjet printer cartridge in lieu of ink. The following list of reagent mixture embodiments was successfully utilized to develop commercial test strips for detection of cardiac heart disease.
　b. Components
　　i. Horseradish Peroxidase (HRP) in PBS 1× (75 U/mL)
　　ii. Cholesterol Oxidase (ChOx or COX) PBS 1× (100 U/mL)
　　iii. Glycerol
　　iv. Dye substrate
　　　1. TMB in Dimethyl sulfoxide (DMSO)
　　　2. 10-Acetyl-3,7-dihydroxyphenoxazine (ADHP) in Dimethyl sulfoxide (DMSO)
　　　3. 4-Aminoantipyrine (AAP) in Phenol
　　　　v. PBS 1×
　c. Reagent mixtures (Glycerol: PBS 1×)
　　i. 2 mL 50:50
　　　1. 100 µL TMB
　　　2. 100 µL HRP
　　　3. 100 µL COX
　　　4. 700 µL PBS 1×
　　　5. 1 mL Glycerol
　　ii. 1 mL 50:50
　　　1. 50 µL TMB
　　　2. 50 µL HRP
　　　3. 50 µL COX
　　　4. 350 µL PBS 1×
　　　5. 500 µL Glycerol
　　iii. 4 mL 50:50
　　　1. 100 µL COX
　　　2. 200 µL HRP
　　　3. 200 µL TMB
　　　4. 1500 µL PBS 1×
　　　5. 1 µL Triton-x-100
　　　6. 2 mL glycerol
　　iv. 2 mL 50:50
　　　1. 100 µL COX
　　　2. 200 HRP
　　　3. 700 PBS 1×
　　　4. 1 mL glycerol
　　v. 250 µL 40:60
　　　1. 50 µL COX
　　　2. 100 µL HRP
　　　3. 100 µL glycerol
　　vi. 250 µL
　　　1. 100 µL glycerol
　　　2. 33 µL HRP
　　　3. 50 µL COX
　　　4. 67 µL PBS 1×
　　vii. 290 µL
　　　1. 50 µL COX
　　　2. 16 µL HRP
　　　3. 108 µL PBS 1×
　　　4. 116 µL glycerol
　　viii. 250 µL 60:40
　　　1. 50 µL COX
　　　2. 16.5 µL HRP
　　　3. 83.5 µL PBS 1×
　　　4. 100 µL glycerol
　　ix. 4 mL 50:50
　　　1. 200 µL HRP
　　　2. 200 µL TMB
　　　3. 200 µL COX
　　　4. 1400 PBS 1×
　　　5. 2 mL glycerol
　　x. 2 mL 50:50
　　　1. 333 µL COX
　　　2. 110 µL HRP
　　　3. 333 µL TMB
　　　4. 224 µL PBS 1×
　　　5. 1 mL glycerol The above reagent ink was then "printed" onto the substrate or solid support in an approximately one centimeter diameter circle. It should be point out that any other shape and size would work just as well. The first layer was then allowed to dry for an hour.

What is claimed is:

1. A method of manufacturing an inexpensive diagnostic test to detect cholesterol and oxidized low-density lipoprotein, comprising: applying a liquid reagent mixture, including a liquid enzyme mixture, glycerol, and color-producing detector reagents, on a substrate using inkjet printing;
- wherein the substrate is passed through an inkjet printer and absorbs the liquid reagent mixture;
  - wherein the inkjet printer contains a cartridge for storing the liquid reagent mixture and a tray to store the substrate;
  - wherein the liquid reagent mixture is of a rheology of high shear thinning liquid dynamics and a specific viscosity to enable jet-stream inkjet processing resulting in high strain rate deformation with dominant extensional behavior;
  - wherein the liquid enzyme mixture contains phosphate-buffered saline solution and a single or multiple enzymatic proteins, including cholesterol oxidase, capable of binding to enzymatic substrates forming enzyme-substrate complexes in which internal dynamic motions of the enzyme catalyze reactions with the enzymatic substrates;
  - wherein glycerol is contained with the liquid reagent mixture to alter the dynamic surface tension of the liquid reagent mixture such that interfacial tension during inkjet printing allows droplet formation;
- wherein the liquid reagent mixture is stored in the cartridge and applied using an inkjet printing system;
- wherein the liquid reagent mixture is applied using the inkjet printer where the cartridge is repurposed for printing diagnostic test strips;
- wherein the cartridge is directly charged, a process in which air, used to pressurize the cartridge, and liquid reagent mixture are injected directly into the cartridge or indirectly charged, a process in which liquid reagent mixture and pressurized air contained externally and injected into the cartridge using a tubing feeder system;
- wherein the liquid reagent mixture is printed as one layer or multiple layers on the substrate using the inkjet printer to form an inexpensive diagnostic test to detect cholesterol and oxidized low-density lipoprotein.

* * * * *